(12) United States Patent
Biedermann et al.

(10) Patent No.: US 6,436,885 B2
(45) Date of Patent: Aug. 20, 2002

(54) ANTIMICROBIAL CLEANSING COMPOSITIONS CONTAINING 2-PYRROLIDONE-5-CARBOXYLIC ACID

(75) Inventors: Kimberly Ann Biedermann, Cincinnati; Jeffrey Michael Morgan, Springboro; Karl Shiqing Wei, Mason, all of OH (US); Mark Richard Sine, Windsor (GB); Cheyne P. Thomas, Highland Heights, KY (US); David Edmund Tarantino, Loveland, OH (US); Christopher Irwin, Cincinnati, OH (US); Christopher Dean Putman, West Chester, OH (US); Peter William Beerse, Morrow, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/738,365

(22) Filed: Dec. 15, 2000

Related U.S. Application Data

(60) Provisional application No. 60/177,092, filed on Jan. 20, 2000, provisional application No. 60/177,091, filed on Jan. 20, 2000, and provisional application No. 60/191,939, filed on Mar. 24, 2000.

(51) Int. Cl.$^7$ ................................................. C11D 1/94
(52) U.S. Cl. ....................................... 510/131; 510/500
(58) Field of Search ............................... 510/131, 132, 510/133, 138, 500

(56) References Cited

U.S. PATENT DOCUMENTS

| | | |
|---|---|---|
| 3,141,821 A | 7/1964 | Compeau et al. ............. 167/58 |
| 3,969,258 A | 7/1976 | Carandang et al. .......... 252/106 |
| 4,075,350 A | 2/1978 | Michaels ..................... 424/316 |
| 4,259,383 A | 3/1981 | Eggensperger et al. ....... 428/72 |
| 4,597,975 A | 7/1986 | Woodward et al. |
| 4,602,099 A | 7/1986 | Parker ......................... 549/479 |
| 4,738,275 A | 4/1988 | Rothe et al. ................. 424/443 |
| 4,738,984 A | 4/1988 | Parker ......................... 514/473 |
| 4,764,418 A | 8/1988 | Kuenn et al. ................ 428/284 |
| 4,767,788 A | 8/1988 | Diana ........................... 514/574 |
| 4,824,689 A | 4/1989 | Kuenn et al. ................... 427/2 |
| 4,828,912 A | 5/1989 | Hossain et al. .............. 428/289 |
| 4,849,221 A | 7/1989 | Marquardt ................... 424/676 |
| 4,891,216 A | 1/1990 | Kross et al. ................... 424/78 |
| 4,897,304 A | 1/1990 | Hossain et al. .............. 428/289 |
| 4,975,217 A | 12/1990 | Brown-Skrobot et al. .. 252/107 |
| 5,098,716 A | 3/1992 | Embro ......................... 424/650 |
| 5,143,720 A | 9/1992 | Lopes ........................... 424/55 |
| 5,280,042 A | 1/1994 | Lopes ........................... 514/557 |
| 5,629,006 A | 5/1997 | Hoang et al. |
| 5,631,218 A | 5/1997 | Allan et al. |
| 5,681,802 A | 10/1997 | Fujiwara et al. ............. 510/130 |
| 5,744,167 A | 4/1998 | Majeti ......................... 424/650 |
| 5,747,070 A | 5/1998 | Majeti ......................... 424/650 |
| 5,830,487 A | 11/1998 | Klofta et al. ................. 424/402 |
| 5,897,891 A | 4/1999 | Godfrey ....................... 426/74 |
| 5,914,300 A | 6/1999 | Fujiwara et al. ............. 510/130 |
| 5,922,764 A | 7/1999 | Cantin et al. ................ 514/557 |
| 6,071,866 A | 6/2000 | Fujiwara et al. ............. 510/130 |
| 6,183,763 B1 | 2/2001 | Beerse et al. |
| 6,197,315 B1 | 3/2001 | Beerse et al. |
| 6,217,887 B1 | 4/2001 | Beerse et al. |

FOREIGN PATENT DOCUMENTS

| | | | |
|---|---|---|---|
| DE | 3832799 A1 | 3/1990 | .......... A61K/31/60 |
| DE | 4137544 A1 | 5/1993 | |
| EP | 0037224 A1 | 10/1981 | ............ C11D/3/48 |
| EP | 0049354 A2 | 4/1982 | .......... A61K/31/19 |
| EP | 0689767 A2 | 1/1996 | |
| EP | 0689767 A3 | 3/1996 | |
| FR | 2656523 A1 | 7/1991 | .......... A61K/7/075 |
| JP | 53052632 | 5/1978 | |
| JP | 07-157415 | 6/1995 | ............ A61K/7/06 |
| JP | 11-263995 | 9/1999 | ............ A61K/7/50 |
| RO | 75422 | 1/1981 | .......... A01N/59/00 |
| SE | 8703-015 A | 2/1989 | .......... A01N/25/34 |
| WO | WO 93/25211 | 12/1993 | ......... A61K/31/765 |
| WO | WO 96/11572 | 4/1996 | .......... A01N/37/02 |
| WO | WO 97/46218 | 12/1997 | ............ A61K/7/48 |
| WO | WO 98/17237 | 4/1998 | ............ A61K/7/16 |
| WO | WO 98/55081 A2 | 12/1998 | |
| WO | WO 98/55094 A1 | 12/1998 | |
| WO | WO 99/55303 | 11/1999 | |
| WO | WO 00/61105 A1 | 10/2000 | |
| WO | WO 00/61105 | 10/2000 | |
| WO | WO 01/28552 A1 | 4/2001 | |
| WO | WO 01/28552 A2 | 4/2001 | |

*Primary Examiner*—John Hardee
(74) *Attorney, Agent, or Firm*—Marianne Dressman; Tara M. Rosnell; Steven W. Miller

(57) ABSTRACT

Disclosed are antimicrobial cleansing compositions that have a pH of from about 2.0 to about 5.5 and comprise an antimicrobial agent, an amphoteric surfactant, and 2-pyrrolidone-5 carboxylic acid as a proton donating agent. Also disclosed are corresponding articles of manufacture and methods of cleansing the skin using the described compositions. The compositions are mild to the skin and provide improved antimicrobial benefits to the skin.

14 Claims, No Drawings

ANTIMICROBIAL CLEANSING COMPOSITIONS CONTAINING 2-PYRROLIDONE-5-CARBOXYLIC ACID

CROSS REFERENCES TO RELATED APPLICATIONS

This application claims the benefit of U.S. Provisional Application Nos. 60/177,092 and 60/177,091, filed on January 20, and 60/191,939, filed on Mar. 24, 2000.

TECHNICAL FIELD

The present invention relates to antimicrobial cleansing compositions comprising an antimicrobial agent, an amphoteric surfactant, and 2-pyrrolidone-5 carboxylic acid, wherein the composition provides immediate and residual antimicrobial activity on the applied areas of the skin. The present invention also relates to corresponding articles of manufacture and methods of cleansing the skin using the compositions of the present invention.

BACKGROUND OF THE INVENTION

Human health is impacted by many microbial entities. Inoculation by viruses and bacteria cause a wide variety of sicknesses and ailments. Media attention to cases of food poisoning, strep infections, and the like is increasing public awareness of microbial issues.

It is well known that the washing of hard surfaces, food (e.g. fruit or vegetables) and skin, especially the hands, with antimicrobial or non-medicated soap, can remove many viruses and bacteria from the washed surfaces. Removal of the viruses and bacteria is due to the surfactancy of the soap and the mechanical action of the wash procedure. Therefore, it is known and recommended that the people wash frequently to reduce the spread of viruses and bacteria.

Bacteria found on the skin can be divided into two groups: resident and transient bacteria. Resident bacteria are Gram positive bacteria which are established as permanent microcolonies on the surface and outermost layers of the skin and play an important, helpful role in preventing the colonization of other, more harmful bacteria and fungi.

Transient bacteria are bacteria which are not part of the normal resident flora of the skin, but can be deposited when airborne contaminated material lands on the skin or when contaminated material is brought into physical contact with it. Transient bacteria are typically divided into two subclasses: Gram positive and Gram negative. Gram positive bacteria include pathogens such as *Staphylococcus aureus, Streptococcus pyogenes* and *Clostridiutn botulinum*. Gram negative bacteria include pathogens such as Salmonella, *Escherichia coli*, Klebsiella, Haemophilius, *Pseudomonas aeruginosa*, Proteus and *Shigella dysenteriae*. Gram negative bacteria are generally distinguished from Gram positive by an additional protective cell membrane which generally results in the Gram negative bacteria being less susceptible to topical antibacterial actives.

Antimicrobial cleansing products have been marketed in a variety of forms for some time. Forms include deodorant soaps, hard surface cleaners, and surgical disinfectants. These traditional rinse-off antimicrobial products have been formulated to provide bacteria reduction during washing. For example, Dial® liquid soaps, when used in hand washing, have been found to reduce the amount of the bacteria on the skin by from about 2.0 log (97%) to about 2.5 log (99.7%) in one 30 second handwash, as measured by standard Health Care Personal Handwash Tests (HCPHWT). That is skin washed with these soaps were contaminated with only 0.3%–3% the number of bacteria compared to before washing. Antimicrobial liquid cleansers are disclosed in U.S. Pat. No. 4,847,072, Bissett et al., issued Jul. 11, 1989, U.S. Pat. No. 4,939,284, Degenhardt, issued Jul. 3, 1990 and U.S. Pat. No. 4,820,698, Degenhardt, issued Apr. 11, 1989, all of which are incorporated herein by reference.

Some of these antimicrobial products, especially the hard surface cleaners and surgical disinfectants, utilize high levels of alcohol and/or harsh surfactants which have been shown to dry out and irritate skin tissues. Dial® bar soap has been found to provide from 2.5 to 3.0 log reduction in bacteria in one wash, as measured by the HCPHWT. However, Dial® can be drying to the skin with repeated use. Hibiclens® Surgical Scrub provides 2.5 to 3.0 log reduction in germs in one wash, however it utilizes a potent cationic antibacterial agent, chlorohexidine, which has product safety concerns. Ideal personal cleansers should gently cleanse the skin, cause little or no irritation, and not leave the skin overly dry after frequent use and preferably should provide a moisturizing benefit to the skin.

Given the health impacts of bacteria like *Staphylococcus aureus, Streptococcus pyogenes* and *Clostridium botulinum*, it would be highly desirable to formulate antimicrobial cleansing products which provides improve germ reduction on the skin, which are mild to the skin and which can be used without water. Existing products have been unable to deliver all of these benefits.

It has now been found that the antimicrobial cleansing compositions of the present invention can be formulated to provide improved mildness to the skin and improved antibacterial, antiviral, and/or antifungal activity, wherein the compositions comprise an antibacterial active, 2-pyrrolidone-5 carboxylic acid, and an amphoteric surfactant, all of which are deposited on the skin. The 2-pyrrolidone-5 carboxylic acid and amphoteric surfactant enhance the selected active, to provide a new level of hostility to bacteria contacting the skin.

SUMMARY OF THE INVENTION

The present invention relates to antimicrobial cleansing compositions, wherein the compositions comprise from about 0.001% to about 5.0% by weight of an antimicrobial active; from about 0.05% to about 10% by weight of an amphoteric surfactant; from about 0.1% to about 10%, by weight of 2-pyrrolidone-5 carboxylic acid; and from about 3% to about 99.89% by weight an aqueous component. The cleansing compositions of the present invention have a pH in the range of about 2.0 to about 5.5. The present invention also relates to articles of manufacture and methods of cleansing the skin comprising the disclosed compositions.

DETAILED DESCRIPTION OF THE INVENTION

The antimicrobial cleansing compositions of the present invention are highly efficacious for providing an improved germ reduction on the skin, are mild to the skin and can be used without additional available water.

The term "safe and effective amount" as used herein means an amount of a compound or composition sufficient to significantly induce a positive benefit, preferably an antimicrobial benefit, but low enough to avoid serious side effects, i.e., to provide a reasonable benefit to risk ratio, within the scope of sound judgment of the skilled artisan.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

The antimicrobial cleansing composition of the present invention comprise the following essential components, which components are selected so that the efficacy and optional mildness requirements hereinafter defined for the compositions herein are preferably met. The selection of each component is necessarily dependent on the selection of each of the other components. If a harsh surfactant is utilized, then a mildness agent may have to be utilized. Guidelines for the selection of the individual components are provided herein.

The Antimicrobial Active

The antimicrobial cleansing composition of the present invention comprise an antimicrobial active at concentrations ranging from about 0.001% to about 5%, preferably from about 0.05% to about 1%, more preferably from about 0.05% to about 0.5%, even more preferably from about 0.1% to about 0.25%, by weight of composition. The exact amount of antibacterial active to be used in the compositions will depend upon factors such as the particular active utilized since actives vary in potency.

Given below are examples of non-cationic antimicrobial agents which are useful in the compositions of the present invention.

Pyrithiones, especially the zinc complex (ZPT)
Benzalkonium Chloride
Di($C_6$–$C_{14}$)alkyl di short chain ($C_{1-4}$ alkyl and/or hydroxyalkyl)
N-(3-chloroallyl) hexaminium chlorides
Benzethonium chloride
Methylbenzethonium
Octopirox®
Dimethyldimethylol Hydantoin (Glydant®)
Methylchloroisothiazolinone/methylisothiazolinone (Kathon CG®)
Sodium Sulfite
Sodium Bisulfite
Imidazolidinyl Urea (Germall 115®)
Diazolidinyl Urea (Germaill II®)
Benzyl Alcohol
2-Bromo-2-nitropropane-1,3-diol (Bronopol®)
Formalin (formaldehyde)
Iodopropenyl Butylcarbamate (Polyphase P100®)
Chloroacetamide
Methanamine
Methyldibromonitrile Glutaronitrile (1,2-Dibromo-2,4-dicyanobutane or Tektamer®)
Glutaraldehyde
5-bromo-5-nitro-1,3-dioxane (Bronidox®)
Phenethyl Alcohol
o-Phenylphenol/sodium o-phenylphenol
Sodium Hydroxymethylglycinate (Suttocide A®)
Polymethoxy Bicyclic Oxazolidine (Nuosept C®)
Dimethoxane
Thimersal
Dichlorobenzyl Alcohol
Captan
Chlorphenenesin
Dichlorophene
Chlorbutanol
Glyceryl Laurate
Halogenated Diphenyl Ethers
   2,4,4'-trichloro-2'-hydroxy-diphenyl ether (Triclosan® or TCS)
   2,2'-dihydroxy-5,5'-dibromo-diphenyl ether Phenolic Compounds
   Phenol
   2-Methyl Phenol
   3-Methyl Phenol
   4-Methyl Phenol
   4-Ethyl Phenol
   2,4-Dimethyl Phenol
   2,5-Dimethyl Phenol
   3,4-Dimethyl Phenol
   2,6-Dimethyl Phenol
   4-n-Propyl Phenol
   4-n-Butyl Phenol
   4-n-Amyl Phenol
   4-tert-Amyl Phenol
   4-n-Hexyl Phenol
   4-n-Heptyl Phenol
Mono- and Poly-Alkyl and Aromatic Halophenols
   p-Chlorophenol
   Methyl p-Chlorophenol
   Ethyl p-Chlorophenol
   n-Propyl p-Chlorophenol
   n-Butyl p-Chlorophenol
   n-Amyl p-Chlorophenol
   sec-Amyl p-Chlorophenol
   n-Hexyl p-Chlorophenol
   Cyclohexyl p-Chlorophenol
   n-Heptyl p-Chlorophenol
   n-Octyl p-Chlorophenol
   o-Chlorophenol
   Methyl o-Chlorophenol
   Ethyl o-Chlorophenol
   n-Propyl o-Chlorophenol
   n-Butyl o-Chlorophenol
   n-Amyl o-Chlorophenol
   tert-Amyl o-Chlorophenol
   n-Hexyl o-Chlorophenol
   n-Heptyl o-Chlorophenol
   o-Benzyl p-Chlorophenol
   o-Benxyl-m-methyl p-Chlorophenol
   o-Benzyl-m, m-dimethyl p-Chlorophenol
   o-Phenylethyl p-Chlorophenol
   o-Phenylethyl-m-methyl p-Chlorophenol
   3-Methyl p-Chlorophenol
   3,5-Dimethyl p-Chlorophenol
   6-Ethyl-3-methyl p-Chlorophenol
   6-n-Propyl-3-methyl p-Chlorophenol
   6-iso-Propyl-3-methyl p-Chlorophenol
   2-Ethyl-3,5-dimethyl p-Chlorophenol
   6-sec-Butyl-3-methyl p-Chlorophenol
   2-iso-Propyl-3,5-dimethyl p-Chlorophenol
   6-Diethylmethyl-3-methyl p-Chlorophenol
   6-iso-Propyl-2-ethyl-3-methyl p-Chlorophenol
   2-sec-Amyl-3,5-dimethyl p-Chlorophenol
   2-Diethylmethyl-3,5-dimethyl p-Chlorophenol
   6-sec-Octyl-3-methyl p-Chlorophenol
   p-Chloro-m-cresol p-Bromophenol
Methyl p-Bromophenol
Ethyl p-Bromophenol
n-Propyl p-Bromophenol
n-Butyl p-Bromophenol
n-Amyl p-Bromophenol
sec-Amyl p-Bromophenol
n-Hexyl p-Bromophenol
Cyclohexyl p-Bromophenol
o-Bromophenol
tert-Amyl o-Bromophenol
n-Hexyl o-Bromophenol
n-Propyl-m,m-Dimethyl o-Bromophenol
2-Phenyl Phenol
4-Chloro-2-methyl phenol
4-Chloro-3-methyl phenol
4-Chloro-3,5-dimethyl phenol
2,4-Dichloro-3,5-dimethylphenol
3,4,5,6-Terabromo-2-methylphenol
5-Methyl-2-pentylphenol
4-Isopropyl-3-methylphenol
Para-chloro-meta-xylenol (PCMX)
Chlorothymol
Phenoxyethanol
Phenoxyisopropanol
5-Chloro-2-hydroxydiphenylmethane
Resorcinol and its Derivatives
   Resorcinol
   Methyl Resorcinol
   Ethyl Resorcinol
   n-Propyl Resorcinol
   n-Butyl Resorcinol
   n-Amyl Resorcinol
   n-Hexyl Resorcinol
   n-Heptyl Resorcinol
   n-Octyl Resorcinol
   n-Nonyl Resorcinol
   Phenyl Resorcinol
   Benzyl Resorcinol
   Phenylethyl Resorcinol
   Phenylpropyl Resorcinol
   p-Chlorobenzyl Resorcinol
   5-Chloro 2,4-Dihydroxydiphenyl Methane
   4'-Chloro 2,4-Dihydroxydiphenyl Methane
   5-Bromo 2,4-Dihydroxydiphenyl Methane
   4'-Bromo 2,4-Dihydroxydiphenyl Methane
Bisphenolic Compounds
   2,2'-Methylene bis (4-chlorophenol)
   2,2'-Methylene bis (3,4,6-trichlorophenol)
   2,2'-Methylene bis (4-chloro-6-bromophenol)
   bis (2-hydroxy-3,5-dichlorophenyl) sulphide
   bis (2-hydroxy-5-chlorobenzyl)sulphide
Benzoic Esters (Parabens)
   Methylparaben
   Propylparaben
   Butylparaben
   Ethylparaben
   Isopropylparaben
   Isobutylparaben
   Benzylparaben
   Sodium Methylparaben
   Sodium Propylparaben
Halogenated Carbanilides
   3,4,4'-Trichlorocarbanilides (Triclocarban® or TCC)
   3-Trifluoromethyl4,4'-dichlorocarbanilide
   3,3',4-Trichlorocarbanilide A more detailed description of suitable antimicrobial agents can be found in U.S. Pat. No. 4,163,800; U.S. Pat. No. 3,152,181; U.S. Pat. No. 5,780,064; and *Remington's pharmaceutical Sciences*, $17^{th}$ ed. (Alfonso R. Gennaro ed., 1985) pp. 1158–1169, which descriptions are incorporated herein by reference.

Another class of antibacterial agents, which are useful in the present invention, are the so-called "natural" antibacterial actives, referred to as natural essential oils. These actives derive their names from their natural occurrence in plants. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, *Hydastis carradenisis, Berberidaceae daceae*, Ratanhiae and *Curcunta longa*. Also included in this class of natural essential oils are the key chemical components of the plant oils which have been found to provide the antimicrobial benefit. These chemicals include, but are not limited to anethol, catechole, camphene, carvacol, eugenol, eucalyptol, ferulic acid, farnesol, hinokitiol, tropolone, limonene, menthol, methyl salicylate, thymol, terpineol, verbenone, berberine, ratanhiae extract, caryophellene oxide, citronellic acid, curcumin, nerolidol and geraniol.

Other suitable antimicrobial actives include antibacterial metal salts. This class generally includes salts of metals in groups 3b–7b, 8 and 3a–5a. Specifically are the salts of aluminum, zirconium, zinc, silver, gold, copper, lanthanum, tin, mercury, bismuth, selenium, strontium, scandium, yttrium, cerium, praseodymiun, neodymium, promethum, samarium, europium, gadolinium, terbium, dysprosium, holmium, erbium, thulium, ytterbium, lutetium and mixtures thereof Preferred antimicrobial actives for use herein include benzalkonium chloride, benzethonium chloride, triclosan, triclocarban, octopirox, PCMX, ZPT, natural essential oils and their key ingredients, and mixtures thereof The most preferred antimicrobial active for use in the compositions of the present invention is Benzalkonium Chloride®.

Amphoteric Surfactant

The antimicrobial cleansing compositions of the present invention comprise an amphoteric surfactant at concentrations ranging from about 0.01% to about 20%, preferably from about 0.05% to about 10%, more preferably from about 0.05% to about 10%, by weight of the cleansing composition.

Amphoteric surfactants useful in the present invention are those having the following general formulae (I) (II), (III), (IV) and (V) and mixtures thereof:

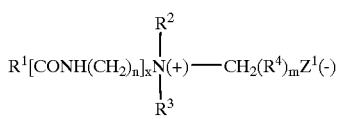

(I)

$$R^1[CONH(CH_2)_n]_x \overset{R^2}{\underset{R^3}{N(+)}} CH_2(R^4)_m Z^1(-)$$

wherein $R^1$ is an alkyl, alkenyl, aryl, or hydroxyalkyl radical of from about 8 to about 22 carbon atoms, optionally interrupted with up to about 10 ethylene oxide moieties and/or 1 glyceryl moiety, $R^2$ and $R^3$ are individually selected from alkyl and monohydroxyalkyl groups containing from about 1 to about 3 carbon atoms, $R^4$ is alkylene, or hydroxyalkylene of from about 1 to about 4 carbon atoms, $Z^1$ is a radical selected from carboxylate, sulfonate, sulfate, phosphate, or phosphonate, x is 0 or 1, n is from about 1 to about 6, and m is 0 or 1. Preferably, $R^1$ is an alkyl, alkenyl, or hydroxyalkyl radical of from 11 to 17 carbon atoms, $R^2$ and $R^3$ are individually selected from alkyl groups containing of from 1 to 3 carbon atoms, $R^4$ is alkylene or hydroxyalkylene of from 1 to 2 carbon atoms, $Z^1$ is a radical selected from carboxylate, sulfonate, x is 0 or 1, n is 1 to 3, and m is 0 or 1.

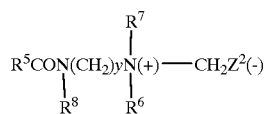

(II)

$$R^5CON(CH_2)y\overset{R^7}{\underset{R^8}{N(+)}}\overset{}{\underset{R^6}{}}CH_2Z^2(-)$$

wherein $R^5$ is $C_8$–$C_{22}$ alkyl, alkenyl, aryl, or hydroxyalkyl, preferably $C_8$–$C_{22}$, $R^6$ is hydrogen or $CH_2CO_2M^1$, $R^7$ is $CH_2CH_2OH$ or $CH_2CH_2OCH_2CH_2COOM^1$, $R^8$ is hydrogen, $CH_2CH_2OH$, or $CH_2CH_2OCH_2CH_2COOM^1$, $Z^2$ is $CO_2M^1$ or $CH_2CO_2M^1$, y is 2 or 3, preferably 2, $M^1$ is hydrogen or a cation, such as alkali metal, alkaline earth metal, ammonium, alkanol ammonium, sulfate, sulfonate, phosphate, or phosphonate.

$$R^9-NH(CH_2)_aCOOM^2 \quad (III)$$

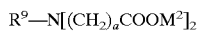

$$R^9-N[(CH_2)_aCOOM^2]_2 \quad (IV)$$

wherein a is a number from 1 to 4, $R^9$ is $C_8$–$C_{22}$ alkyl, alkenyl, aryl, hydroxyalkyl or alkylamidoalkyls, and $M^2$ is hydrogen, alkali metal, alkaline earth metal, ammonium or alkanolammonium.

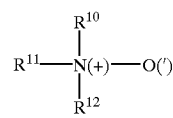

(V)

$$R^{11}-\overset{R^{10}}{\underset{R^{12}}{N(+)}}-O(')$$

wherein $R^{10}$ or $R^{12}$ is methyl, ethyl, or hydroxyethyl, and $R^{11}$ is $C_8$–$C_{22}$ alkyl, alkenyl, or aryl, or $CH_3(CH_2)pCONH(CH_2)q$ wherein p is 8–22 and q is 1–6. Preferably, $R^{10}$ and $R^{12}$ are methyl, $R^{11}$ is $C_{10\text{-}18}$ alkyl, alkenyl, p is 11–17, and q is 1–3.

Examples of amphoteric surfactants useful in the antimicrobial cleansing compositions having general formula (I) are amide betaines, amide sulfo betaines, alkyl betaines, alkenyl betaines, sultaines (sulfo betaines), and imidazolinium betaines. Examples of amphoteric surfactants particularly useful are high alkyl betaines, such as coco dimethyl carboxymethyl betaine, cocamidopropyl betaine under the trade name of TEGO BETAINE, coco betaine, lauryl betaine under the trade name REWOTERIC AM DML-35, lauryl amidopropyl betaine, oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, cocamidopropyl hydroxy sultaine (sulfobetaine), lauryl sultaine (lauryl sulfobetaine), and cocamidopropyl hydroxy sultaine under the trade name REWOTERIC AM CAS.

Examples of amphoteric surfactants useful in the antimicrobial cleansing compositions having general formula (II) are marketed under the trade name MIRANOL and are understood to comprise a complex mixture of species, and can exist in protonated and non-protonated species depending upon pH with respect to species that can have a hydrogen at $R^6$. The imidazolinium amphoteric surfactant hereof can be derived via an imidazolinium intermediate.

Preferred amphoteric surfactants of formula (II) are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Specific commercial products providing the imidazolinium derivative component of the present compositions include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIP (Alkaril Chemicals); cocoamphocarboxy propionate under the trade name NIKKOL AM-101, AMPHOTERGE W-2 (Lonza, Inc.); MONATERIC CDX-38, MONATERIC CSH-32 (Mona Industries); REWOTERIC AM-2C (Rewo Chemical Group); and SCHEROTERIC MS-2 (Scher Chemicals).

Examples of amphoteric surfactants useful in the antimicrobial cleansing compositions having general formulae (III) and (IV) include n-alkylaminopropionates and n-alkyliminodipropionates. Such materials are sold under the trade name DERIPHAT by Henkel and MIRATAINE by Miranol, Inc. Specific examples include N-lauryl-beta-amino propionic acid or salts thereof, and N-lauryl-beta-imino-dipropionic acid or salts thereof.

Examples of amphoteric surfactants useful in the antimicrobial cleansing compositions having general formula (V) are commonly known as amine oxides. Also useful are tertiary phosphine oxides and dialkyl sulfoxides. Mixtures of the above amphoteric surfactants can also be used.

The most preferred amphoteric surfactants are amine oxides. Examples of amine oxides particularly useful in the antimicrobial cleansing compositions are cocamine oxide, lauramine oxide under the trade name AMMONYX LO, and stearamidopropylamine oxide under the trade name VAROX 1770.

2-pyrrolidone-5 Carboxylic Acid

The antimicrobial cleansing compositions of the present invention comprise 2-pyrrolidone-5 carboxylic acid as a proton donating agent at concentrations ranging from about 0.1% to about 20%, preferably from about 0.1% to about 10%, more preferably from about 0.5% to about 8%, and most preferably from about 1% to about 5%, by weight of the composition.

The term "proton donating agent" as used herein refers to the 2-pyrrolidone-5 carboxylic acid component of the cleansing compositions that is ultimatile applied topically to the skin and that results in undissociated acid on the applied area of the skin after application. This particular proton donating agent remains at least partially undissociated in the neat composition and when the compositions are diluted during washing and rinsing. This particular proton donating agent can be added directly to the cleansing composition in the acid form or can be formed by adding the conjugate base of the desired acid and a sufficient amount of a separate acid strong enough to form the undissociated acid from the base.

Composition pH

It is critical to achieving the benefits of the invention that the undissociated acid from the selected proton donating agent (2-pyrrolidone-5 carboxylic acid as deposited or formed in-situ) remain on the skin in the protonated form. Therefore, the pH of the cleansing compositions of the present invention must be adjusted to a sufficiently low level in order to either form or deposit substantial undissociated acid on the skin. The pH of the compositions should be adjusted and preferably buffered to range from about 2.0 to about 5.5, preferably from about 2.5 to about 5.0 and more preferably from about 2.5 to about 4.5.

It has been found that 2-pyrrolidone-5 carboxylic acid as the selected proton donating agent in the compositions of the present invention is milder to the skin and causes less stinging than many other acids that are likewise suitable for topical application to the skin.

Aqueous Component

The cleansing compositions described herein additionally comprise an aqueous component. For purposes of this invention the term "aqueous component" refers to any material consisting essentially of, or predominantly of water, water soluble alcohol(s) such as ethanol, propanol or isopropanol, and mixtures thereof.

The aqueous component can optionally contain one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

The aqueous component is preferably water which is deionized, distilled or purified. Preferred cleansing compositions comprise from about 3% to about 99%, preferably from about 5% to about 98%, more preferably from about 10% to about 97.5%, and most preferably from about 38% to about 95.99%, by weight of the aqueous component.

Preferable Optional Ingredients

Mildness Enhancers

In order to achieve the mildness required of the present invention, optional ingredients to enhance the mildness to the skin can be added. These ingredients include cationic and nonionic polymers, co-surfactants, moisturizers and mixtures thereof. Polymers useful herein include polyethylene glycols, polypropylene glycols, hydrolyzed silk proteins, hydrolyzed milk proteins, hydrolyzed keratin proteins, guar hydroxypropyltrimonium chloride, polyquats, silicone polymers and mixtures thereof. When used, the mildness enhancing polymers comprise from about 0.1% to about 1%, preferably from about 0.2% to about 1.0%, and more preferably from about 0.2% to about 0.6%, by weight of the antimicrobial cleansing composition, of the composition. Co-surfactants useful herein include nonionic surfactants such as the Genapol® 24 series of ethoxylated alcohols, POE(20) sorbitan monooleate (Tween® 80), polyethylene glycol cocoate and Pluronic® propylene oxide/ethylene oxide block polymers, and amphoteric surfactants such as alkyl betaines, alkyl sultaines, alkyl amphoacetates, alkyl amphodiacetates, alkyl amphopropionates, and alkyl amphodipropionates. When used, the mildness enhancing co-surfactants comprise from about 20% to about 70%, preferably from about 20% to about 50%, by weight of the amphotericsurfactant, of the cleansing composition.

Another group of mildness enhancers are lipid skin moisturizing agents which provide a moisturizing benefit to the user of the cleansing composition when the lipophilic skin moisturizing agent is deposited to the user's skin. When used in the antimicrobial personal cleansing compositions herein, lipophilic skin moisturizing agents are used, they are employed at a level of about 0.1% to about 30%, preferably from about 0.2% to about 10%, most preferably from about 0.5% to about 5% by weight of the composition.

In some cases, the lipophilic skin moisturizing agent can desirably be defined in terms of its solubility parameter, as defined by *Vaughan in Cosmetics and Toiletries*, Vol. 103, p. 47–69, October 1988. A lipophilic skin moisturizing agent having a Vaughan solubility Parameter (VSP) from 5 to 10, preferably from 5.5 to 9 is suitable for use in the antimicrobial cleansing compositions herein.

A wide variety of lipid type materials and mixtures of materials are suitable for use in the antimicrobial cleansing compositions of the present invention. Preferably, the lipophilic skin conditioning agent is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils such as those described in U.S. Pat. No. 3,600,186 to Mattson; Issued Aug. 17, 1971 and U.S. Pat. Nos. 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797,300 to Jandacek; issued Jan. 10, 1989; U.S. Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk tri-glycerides, wax esters, beeswax derivatives, sterols, phospholipids and mixtures thereof. Fatty acids, fatty acid soaps and water soluble polyols are specifically excluded from our definition of a lipophilic skin moisturizing agent.

Hydrocarbon oils and waxes: Some examples are petrolatum, mineral oil microcrystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratioof petrolatum to polybutene ranges from about 90:10 to about 40:60 are also suitable for use as the lipid skin moisturizing agent in the compositions herein.

Silicone Oils: Some examples are dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof. Nonlimiting examples of silicones useful herein are described in U.S. Pat. No. 5,011,68 1, to Ciotti et al., issued Apr. 30, 1991, which is incorporated by reference.

Di- and tri-glycerides: Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetoglyceride esters are used and an example is acetylated monoglycerides.

Lanolin and its derivatives are preferred and some examples are lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate.

It is most preferred when at least 75% of the lipophilic skin conditioning agent is comprised of lipids selected from the group consisting: petrolatum, blends of petrolatum and high molecular weight polybutene, mineral oil, liquid non-digestible oils (e.g. liquid cottonseed sucrose octaesters) or blends of liquid digestible or nondigestible oils with solid polyol polyesters (e.g. sucrose octaesters prepared from C22 fatty acids) wherein the ratio of liquid digestible or nondigestible oil to solid polyol polyester ranges from about 96:4 to about 80:20, hydrogenated or nonhydrogenated polybutene, microcrystalline wax, polyalkene, paraffin, cerasin, ozokerite, polyethylene, perhydrosqualene; dimethicones, alkyl siloxane, polymethylsiloxane, methylphenylpolysiloxane and mixtures thereof. When as blend of petrolatum and other lipids is used, the ratio of petrolatum to the other selected lipids (hydrogenated or unhydrogenated polybutene or polydecene or mineral oil) is preferably from about 10:1 to about 1:2, more preferably from about 5:1 to about 1:1.

Degreasing and/or Detackifying Agent

Also essential to the compositions of the present invention are degreasing and/or detackifying agents in an effective amount to reduce the greasy feel or stickiness associated with the lipophilic skin moisturizers. The term "degreasing agent," as used herein, means an agent which prevents, reduces and/or eliminates the greasy or heavy skin feel typically associated with lipophilic materials. The term "detackifying agent," as used herein, means an agent which prevents, reduces and/or eliminates the sticky or tacky geeling typically associated with ingredients such as humectants. Degreasing or detackifying agents suitable for use in the present invention are selected from the group consisting of select silicones, wax materials soluble in the alcoholic antiseptic and having a melting point greater than about 20° C., powders, fluorochemicals and mixtures thereof.

i) Silicones

Useful as degreasing agents in the present invention are volatile and non-volatile silicone oils. The term "nonvolatile" as used herein means that the silicone has a boiling point of at least about 260° C., preferably at least about 275° C., more preferably at least about 300° C. Such materials exhibit very low or no significant vapor pressure at ambient conditions. The term "volatile" as used herein mean that the silicone has a boiling point of from about 99° C. to about 260° C.

Volatile silicones suitable for use in the present invention are disclosed in U.S. Pat. No. 4,781,917, issued to Luebbe et al., Nov. 1, 1988 and U.S. Pat. No. 5,759,529 to LeGrow et al., issued Jun. 2, 1998, both of which are herein incorporated by reference in their entirety. Additionally, a description of various volatile silicones materials is found in Todd et al., "Volatile Silicone Fluids for Cosmetics", Cosmetics and Toiletries, 91:27–32 (1976). Preferred silicones have surface tensions of less than about 35 dynes, more preferably less than about 30 dynes, most preferably less than about 25 dynes. Particularly preferred volatile silicone oils are selected from the group consisting of cyclic volatile silicones corresponding to the formula:

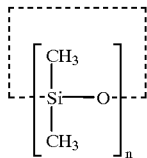

wherein n is from about 3 to about 7; and linear volatile silicones corresponding to the formula:

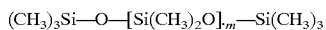

wherein m is from about 1 to about 7. Linear volatile silicones generally have a viscosity of less than about 5 centistokes at 25.degree. C., whereas the cyclic silicones have viscosities of less than about 10 centistokes at 25.degree. C. Highly preferred examples of volatile silicone oils include cyclomethicones of varying viscosities, e.g., Dow Corning 200, Dow Corning 244, Dow Corning 245, Dow Coming 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.). When present in the compositions of the present invention, volatile silicones comprise at least about or greater than about 3% to about 10%, more preferably from about 4% to about 8%, and most preferably from about 6% to about 8% by weight of the present invention.

Also useful as the degreasing agent are nonvolatile silicones such as fluid silicones and gum silicones. The molecular weight and viscosity of the particular selected silicone will determine whether it is a gum or a fluid. The term "silicone fluid," as used herein, denotes a silicone with viscosities ranging from about 5 to about 600,000 centistokes, most preferably from about 350 to about 100,000 centistokes, at 25° C. The term "silicone gum," as used herein, denotes silicones with mass molecular weights of from about 200,000 to about 1,000,000 and with viscosities greater than about 600,000 centistokes. The non-volatile silicones of the present invention preferably have a viscosity of at least about 15,000 centipoise, more preferably at least 25,000 centipoise.

Suitable non-volatile silicones include polysiloxanes and other modified silicones. Polysiloxanes and other modified silicones are described in U.S. Pat. Nos. 5,650,144 and 5,840,288, both of which are herein incorporated by reference in their entirety. Examples of suitable polysiloxanes and modified silicones include, but are not limited to, polyalkylsiloxanes, polyarylsiloxanes, polyalkylarylsiloxanes, polyestersiloxanes, polyethersiloxane copolymers, polyfluorosiloxanes, polyaminosiloxanes, and mixtures thereof. Preferred non-volatile polysiloxanes are polydimethylsiloxane having viscosities of from about 5 to about 100,000 centistokes at 25° C.

Silicone fluid and gum mixtures or blends can also be used. Silicone gum and fluid blends are disclosed in U.S. Pat. No. 4,906,459, Cobb et al., issued Mar. 6, 1990; U.S. Pat. No. 4,788,006, Bolich, Jr. et al., issued Nov. 29, 1988; U.S. Pat. No. 4,741,855, Grote et al., issued May 3, 1988; U.S. Pat. No. 4,728,457, Fieler et al., issued Mar. 1, 1988;

U.S. Pat. No. 4,704,272, Oh et al., issued Nov. 3. 1987; and U.S. Pat. No. 2,826,551, Geen, issued Mar. 11, 1958; U.S. Pat. No. 5,154,849, Visscher et al., issued Oct. 13, 1992, all of which are herein incorporated by reference in their entirety.

When present in the compositions of the present invention, non-volatile silicones comprise from about 0.01% to about 5%, preferably from about 0.1% to about 2%, more preferably from about 0.1% to about 1% by weight of the present invention.

Silicone elastomers are also useful as degreasing agents in the present invention. Suitable silicone elastomers are illustrated in U.S. Pat. No. 5,654,362, herein incorporated by reference in its entirety. Examples of suitable elastomers include, but are not limited to, dimethicone crosspolymer, dimethicone/vinyidimethicone crosspolymer, polysilicone-11 and mixtures thereof. Such elastomers can be used alone or with volatile or nonvolatile solvents. Examples of suitable solvents include, but are not limited to, volatile silicones, volatile alcohols, volatile esters, volatile hydrocarbons, and mixtures thereof. The silicone elastomers are crosslinked and preferably have a weight average molecular weight greater than about 100,000. Preferred for use herein are elastomer/solvent blends having an elastomer to solvent ratio of from about 1:100 to about 1:1, more preferably from about 1:30 to about 1:5. Preferably the silicone elastomer blend has a viscosity of from about 50,000 centipoise to about 400,000 centipoise, more preferably from about 100,000 centipoise to about 300, 000 centipoise.

Examples of suitable silicone elastomer blends include cyclomethicone and dimethicone crosspolymer blend (Dow Corning®9040 silicone elastomer); cyclomethicone and dimethicone/vinyidimethicone cross polymer blend (SFE 839 elastomer dispersion available from GE); octamethyl-cyclotetrasiloxane and polysilicone-11 blend (Gransil GCM available from Shin Etsu); and mixtures thereof. Preferred herein is the cyclomethicone and dimethicone/vinyidimethicone cross polymer blend.

When present, the silicone elastomer preferably comprises from about 0.01% to about 5%, preferably from about 0.1% to about 2%.

When present, silicone elastomer or gum blends preferably comprise from about 0.1% to about 10%, preferably from about 1% to about 10%, most preferably from about 4% to about 10% by weight of the composition.

ii.) Wax Materials

Wax materials used herein preferably have melting points of at least about or greater than about 20° C., more preferably at least about or greater than about 25° C., and still more preferably at least about or greater than 32° C., and most preferably at least about or greater than about 35° C. The wax materials are preferably soluble in the alcohol antiseptic. The phrase "soluble in the alcohol antiseptic," as used herein, means the wax materials is soluble in the alcohol antiseptic, at 25° C., at a concentration of 0.1%, preferably 0.2%, more preferably 0.4% by weight, and most preferably soluble at 1.0% by weight. Examples of suitable wax materials include, but are not limited to, dimethicone copolyols having a weight average molecular weight greater than about 1000 such as Biowax®.(supplied by Biosil), polyoxyethylene glycols having weight average molecular weight greater than about 500 such as Carbowax (supplied by Union Carbide), and mixtures thereof. Preferred for use herein is Biowax® 754.

Also preferred for use herein are polyoxyethylene glycols having weight average molecular weight greater than about 500, preferably from about 1000 to about 10,000, more preferably from about 1400 to about 6000. Most preferred is PEG-32 (Carbowax 1450).

When present, the above wax materials preferably comprise from about 0.1% to about 10%, preferably from about 0.1% to about 5%, most preferably from about 0.4% to about 2% by weight of the composition.

iii.) Powders

Also useful as degreasing agents are powders. Powder ingredients which may be compounded in the composition of the present invention include inorganic powder such as gums, chalk, Fuller's earth, talc, kaolin, iron oxide, mica, sericite, muscovite, phlogopite, synthetic mica, lepidolite, biotite, lithia mica, vermiculite, magnesium carbonate, calcium carbonate, aluminum silicate, starch, smectite clays, alkyl and/or trialkyl aryl ammonium smectites, chemically modified magnesium aluminum silicate, organically modified montmorillonite clay, hydrated aluminum silicate, fumed silica, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, polyethylene powder, methyl polymethacrylate powder, polystyrene powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as titanium dioxide, zinc oxide, and magnesium oxide. Other useful powders are disclosed in U.S. Pat. No. 5, 688,831, to El-Nokaly et al., issued Nov. 18, 1997, herein incorporated by reference in its entirety. Preferred for use herein are particulate crosslinked hydrocarbyl-substituted polysiloxane available under the tradename Tospearl from Toshiba Silicone. Mixtures of the above powders may also be used.

Preferably the powders of the present invention have a particle size such that the average chord length of the powder particles range from about 0.01 microns to about 100 microns, preferably from about 0.1 microns to about 50 microns, more preferably from about 1 micron to about 20 microns.

Preferably, the powders of the present invention are spherical or platelet in shape for smooth skin feel. Alternatively and preferably, the powders can by amorphous or irregular shaped for a draggy skin feel. When present, powders preferably comprise from about 0.01% to about 10%, preferably from about 0.1% to about 10%, more preferably from about 0.1% to about 5%, most preferably from about 0.4% to about 2% by weight of the composition.

iv.) Fluorochemicals

Also useful herein are fluorochemicals. These fluorochemicals include fluorotelemers, and perfluoropolyethers, some examples of which are described in Cosmetics & Toiletries, Using Fluorinated Compounds in Topical Preparations, Vol. 111, pages 47–62, (October 1996) which description is incorporated herein by reference. More specific examples of such liquid carriers include, but are not limited to, perfluoropolymethyl isopropyl ethers, perfluoropolypropylethers, acrylamide fluorinated telomer or mixtures thereof. Other more specific examples include, but are not limited to, the polyperfluoroisopropyl ethers available from Dupont Performance Chemicals under the trade name Fluortress® PFPE oils.

When present, powders preferably comprise from about 0.01% to about 10%, preferably from about 0. 1% to about 2% by weight of the composition.

Whilst some materials can function either as the lipophilic skin moisturizing agent, thickening agent therefor, or degreasing or detackifying agent, it will be appreciated that the moisturizing, thickening and decreasing or detackifying function cannot be provided by the same component. However, it will be understood that where the composition comprises three or more lipophilic skin moisturizing agents, two of said lipophilic skin moisturizing agents can also function as a thickening agent, or degreasing or detackifying agent.

When a lipophilic skin moisturizing agent is employed as the mildness enhancer in the antimicrobial compositions herein, a stabilizer may also be included at a level ranging from about 0.1% to about 10%, preferably from about 0.1% to about 8%, more preferably from about 0.1% to about 5% by weight of the antimicrobial cleansing composition.

The stabilizer is used to form a crystalline stabilizing network in the liquid cleansing composition that prevents the lipophilic skin moisturizer agent droplets from coalescing and phase splitting in the product. The network exhibits time dependent recovery of viscosity after shearing (e.g., thixotropy).

The stabilizers used herein are not surfactants. The stabilizers provide improved shelf and stress stability. Some preferred hydroxyl-containing stabilizers include 12-hydroxystearic acid, 9,10-dihydroxystearic acid, tri-9, 10-dihydroxystearin and tri-12-hydroxystearin (hydrogenated castor oil is mostly tri-12-hydroxystearin). Tri-12-hydroxystearin is most preferred for use in the compositions herein. When these crystalline, hydroxyl-containing stabilizers are utilized in the cleansing compositions herein, they are typically present at from about 0.1% to 10%, preferably from 0.1% to 8%, more preferably from 0.1% to about 5% of the antimicrobial cleansing compositions. The stabilizer is insoluble in water under ambient to near ambient conditions.

Alternatively, the stabilizer employed in the cleansing compositions herein can comprise a polymeric thickener. When polymeric thickeners as the stabilizer in the cleansing compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000, anionic, cationic, and nonionic homopolymers derived from acrylic and/or methacrylic acid, anionic, cationic, and nonionic cellulose resins, cationic copolymers of dimethyldialkylammonium chloride, and acrylic acid, cationic homopolymers of dimethylalkylammonium chloride, cationic polyalklene and ethoxypolyalkylene imines, polyethylene glycol of molecular weight from 100,000 to 4,000,000, and mixtures thereof. Preferably, the polymer is selected from the group consisting of sodium polyacrylate, hydroxy ethyl cellulose, cetyl hydroxy ethyl Cellulose, and Polyquaternium 10.

Alternatively, the stabilizer employed in the cleansing compositions herein can comprise C10–C22 ethylene glycol fatty acid esters. C10–C22 ethylene glycol fatty acid esters can also desirably be employed in combination with the polymeric thickeners hereinbefore described. The ester is preferably a diester, more preferably a C14–C18 diester, most preferably ethylene glycol distearate. When C10–C22 ethylene glycol fatty acid esters are utilized as the stabilizer in the personal cleansing compositions herein, they are typically present at from about 3% to about 10%, preferably from about 5% to about 8%, more preferably from about 6% to about 8% of the personal cleansing compositions.

Another class of stabilizer which can be employed in the antimicrobial cleansing compositions of the present invention comprises dispersed amorphous silica selected from the group consisting of fumed silica and precipitated silica and mixtures thereof. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. Precipitated silicas and silica gels are generally made in aqueous solution. See, Cabot Technical Data Pamphlet TD-100 entitled "CAB-O-SIL® Untreated Fumed Silica Properties and Functions", October 1993, and Cabot Technical Data Pamphlet TD-104 entitled "CAB-O-SIL® Fumed Silica in Cosmetic and Personal Care Products", March 1992, both of which are herein incorporated by reference.

The fumed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m./gram, most preferably greater than about 180 sq. m./gram.

When amorphous silicas are used as the stabilizer herein, they are typically included in the cleansing compositions at levels ranging from about 0.1% to about 10%, preferably from about 0.25% to about 8%, more preferably from about 0.5% to about 5%.

A fourth class of stabilizer which can be employed in the antimicrobial cleansing compositions of the present invention comprises dispersed smectite clay selected from the group consisting of bentonite and hectorite and mixtures thereof. Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and flourine. See Merck Index, eleventh Edition, 1989, entry 4538, p. 729, which is herein incorporated by reference.

When smectite clay is employed as the stabilizer in the cleansing compositions of the present invention, it is typically included in amounts ranging from about 0.1% to about 10%, preferably from about 0.25% to about 8%, more preferably from about 0.5% to about 5%.

Other known stabilizers, such as fatty acids and fatty alcohols, can also be employed in the compositions herein. Palmitic acid and lauric acid are especially preferred for use herein.

Other Optional Ingredients

The compositions of the present invention can comprise a wide range of optional ingredients. The *CTFA International Cosmetic Ingredient Dictionary*, Sixth Edition, 1995, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

Water-Insoluble Substrates

The compositions of the present invention can also be, optionally, incorporated into a insoluble substrate for application to the skin such as in the form of a treated wipe. Suitable water insoluble substrate materials and methods of manufacture are described in Riedel, "Nonwoven Bonding Methods and Materials," *Nonwoven World* (1987); *The Encyclopedia Americana*, vol. 11, pp. 147–153. vol. 21, pp. 376–383, and vol. 26, pp. 566–581 (1984); U.S. Pat. No. 3,485,786 to Evans, issued Dec. 23, 1969; U.S. Pat. No. 2,862,251, to Kalwarres; U.S. Pat. No. 3,025,585, Kalwarres; U.S. Pat. No. 4,891,227, to Thaman et al., issued Jan. 2, 1990; and U.S. Pat. No. 4,891,228 and U.S. Pat. No. 5,686,088 to Mitra et al., issued Nov. 11, 1997; U.S. Pat. No. 5,674,591; James et al; issued Oct. 7, 1997; all of which are herein incorporated by reference in their entirety.

Nonwoven substrates made from synthetic materials useful in the present invention can also be obtained from a wide variety of commercial sources. Nonlimiting examples of suitable nonwoven layer materials useful herein include PGI Miratec Herringbone, a patterned hydroentangled material containing about 30% rayon and 70% polyester, and having a basis weight of about 56 grams per square yard (gsy), available from PGI/Chicopee, Dayton N.J.; PGI Miratec Starburst, a patterned hydroentangled material containing about 30% rayon and 70% polyester, and having a basis weight of about 56 grams per square yard (gsy), available from PGI/Chicopee, Dayton N.J.; Novonet$^R$ 149–616, a thermo-bonded grid patterned material containing about 100% polypropylene, and having a basis weight of about 50 gsy, available from Veratec, Inc., Walpole, Mass.; Novonet$^R$ 149–801, a thermo-bonded grid patterned material containing about 69% rayon, about 25% polypropylene, and about 6% cotton, and having a basis weight of about 75 gsy, available from Veratec, Inc. Walpole, Mass.; Novonet$^R$ 149–191, a thermo-bonded grid patterned material containing about 69% rayon, about 25% polypropylene, and about 6% cotton, and having a basis weight of about 100 gsy, available from Veratec, Inc. Walpole, Mass.; HEF Nubtex$^R$ 149–801, a nubbed, apertured hydroentangled material, containing about 100% polyester, and having a basis weight of about 70 gsy, available from Veratec, Inc. Walpole, Mass.; Keybak$^R$ 951V, a dry formed apertured material, containing about 75% rayon, about 25% acrylic fibers, and having a basis weight of about 43 gsy, available from PGI/Chicopee, Dayton, N.J.; Keybak$^R$ 1368, an apertured material, containing about 75% rayon, about 25% polyester, and having a basis weight of about 39 gsy, available from PGI/Chicopee, Dayton, N.J.; Duralace$^R$ 1236, an apertured, hydroentangled material, containing about 100% rayon, and having a basis weight from about 40 gsy to about 115 gsy, available from PGI/Chicopee, Dayton, N.J.; Duralace$^R$ 5904, an apertured, hydroentangled material, containing about 100% polyester, and having a basis weight from about 40 gsy to about 115 gsy, available from PGI/Chicopee, Dayton, N.J.; Sontara 8877, an apertured hydroentangled material, containing about 50% Nylon and about 50% Pulp, and having a basis weight of about 68 gsm, available from Dupont Chemical Corp.

Alternatively, the water insoluble substrate can be a polymeric mesh sponge as described in U.S. Pat. No. 5,650,384, incorporated by reference herein in its entirety. The polymeric sponge comprises a plurality of plies of an extruded tubular netting mesh prepared from a strong flexible polymer, such as addition polymers of olefin monomers and polyamides of polycarboxylic acids. Although these polymeric sponges are designed to be used in conjunction with a liquid cleanser, these types of sponges can be used as the water insoluble substrate in the present invention.

Methods for Cleansing and Disinfecting the Skin

The skin antimicrobial cleansing compositions of the present invention are useful for disinfecting and cleansing the skin. Generally, the skin disinfection and cleansing process involves topically applying to the skin a safe and effective amount of a composition of the present invention. The present invention can be used when cleansing processes requiring soap and water are unavailable or inconvenient. The amount of the composition applied, the frequency of application and the period of use will vary widely depending upon the level of disinfection and cleansing desired, e.g., the degree of microbial contamination and/or skin soiling. Typical amounts of antimicrobial cleansing composition used preferably range from about 0.1 mg/cm$^2$ to about 20 mg/cm$^2$, more preferably from about 0.5 mg/cm$^2$ to about 10 mg/cm$^2$, and most preferably about 1 mg/ cm$^2$ to about 5 mg/cm$^2$ of skin area to be cleansed. Preferably, the antimicrobial cleansing compositions of the present invention are used to cleanse and disinfect human and/or animal skin.

The present invention also encompasses the method of applying an effective amount of the antimicrobial cleansing compositions of the present invention onto non-skin surfaces, such as household surfaces, e.g., countertops, kitchen surfaces, food preparing surfaces (cutting boards, dishes, pots and pans, and the like); major household appliances, e.g., refrigerators, freezers, washing machines, automatic dryers, ovens, microwave ovens, dishwashers; cabinets; walls; floors; bathroom surfaces, shower curtains; garbage cans and/or recycling bins, and the like.

Article of Manufacture

The present invention also relates to an article of manufacture comprising a dispensing container containing the antimicrobial cleansing composition. Said dispensing container can be constructed of any of the conventional material employed in fabricating containers, including, but not limited to: polyethylene; polypropylene; polyacetal; polycarbonate; polyethyleneterephthalate; polyvinyl chloride; polystyrene; blends of polyethylene, vinyl acetate, and rubber elastomer. Other materials can include stainless steel and glass. A preferred container is made of clear material, e.g., polyethylene terephthalate.

Also preferred is an article of manufacture wherein the dispensing container is a spray dispenser. Said spray dispenser is any of the manually activated means for producing a spray of liquid droplets as is known in the art. A preferred spray container is made of clear material, e.g., polyethylene terephthalate.

Preparation of the Substrate Material impregnated with antimicrobial Cleansing Composition Any method suitable for the application of aqueous or aqueous/alcoholic impregnates, including flood coating, spray coating or metered dosing, can be used to impregnate the fibrous webs herein with the antimicrobial cleansing compositions described herein. More specialized techniques, such as Meyer Rod, floating knife or doctor blade, which are typically used to impregnate liquids into absorbent sheets may also be used.

The emulsion should preferably comprise from about 100% to about 400%, preferably from about 100% to about 300% by weight of the absorbent sheet.

After coating, the sheets may be folded into stacks and packaged in any of the moisture and vapor impermeable packages known in the art.

The anti-microbial cleansing compositions of the present invention are made via art recognized techniques for the various forms compositions.

Methods of Using the Antimicrobial Cleansing Wipes

The antimicrobial cleansing compositions and wipe of the present invention are useful for personal cleansing, reducing germs on skin, and providing residual effectiveness versus microorganisms such as fungus and bacteria as well as viruses. Typically the wipe is used to apply the antimicrobial cleansing compositions to the area to be cleansed. The wipes herein can be used for personal cleansing when the use of cleansing products requiring water cannot be, or are inconvenient. Typical quantities of the present wipes useful for cleansing, range from about 1 to about 4 wipes per use, preferably from about 1 to about 2 wipes per use. Typical amounts of antimicrobial cleansing composition used range from about 4 mg/cm$^2$ to about 6 mg/cm$^2$, preferably about 5 mg/cm$^2$ of skin area to be cleansed.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name.

Example 1

The following is an example of a water-insoluble substrate useful in the present invention.

A patterned hydroentangled non-woven substrate having a basis weight of 56 gms, comprising 70% polyester and 30% rayon approximately 6.5 inches wide by 7.5 inches long with a caliper of about 0.80 mm. Optionally, the substrate can be pre-coated with dimethicone (Dow Corning 200 Fluid 5cst) using conventional substrate coating techniques.

Example 2

An aqueous lotion was made based on the following composition:

| Ingredient | Amount (weight percent) |
| --- | --- |
| Benzalkonioum Chloride (Alkaquat DMB-451) | 0.1 |
| Cocamine Oxide (C10/C16 alkyl dimethyl amine oxide; AO-1214 LP supplied by Procter & Gamble Co.) | 0.5 |
| Pyroglutamic Acid (pidolidone) (2-pyrrolidone-5 carboxylic acid) | 4 |
| Ethanol - denatured 200 proof (SD alcohol 40) | 10 |
| DC Antiform H-10 (dimethicone) | 0.03 |
| Sodium Benzoate | 0.2 |
| Tetrasodium EDTA (Hampene 220) | 0.1 |
| Sodium Chloride | 0.4 |
| Perfume | 0.01 |
| Water and minors | q.s. |
| NaOH or HCl for pH adjustment to pH = 3.0 | |

In a suitable container, the pyroglutamic acid, sodium chloride and water are added and mixed with stirring until mixture is homogeneous. Sodium benzoate, tetrasodium EDTA and cocamine oxide are then added to the mixture with stirring and mixed until the ingredients are completely dissolved. Once dissolved, the benzalkonium chloride and DC Antiform H-10 are added to the mixture with stirring. In a separate container, the perfume and ethanol are mixed to form a premix. The premix is then added to the benzalkonium chloride mixture to form the aqueous lotion. The aqueous lotion is pH adjusted to about 3.0 using NaOH or HCl. The aqueous lotion is applied to the skin in an appropriate amount to disinfect and cleanse the skin.

Alternatively, the aqueous lotion can be applied onto the substrate of Example 1 at a lotion to wipe weight ratio of about 2:1 using conventional substrate coating techniques for application to the skin as an antimicrobial and cleansing wipe.

Example 3

An aqueous lotion was made based on the following composition:

| Ingredient | Amount (weight percent) |
| --- | --- |
| Benzalkonioum Chloride | 0.1 |
| Ammonium Lauryl Sulfate | 0.6 |
| Pyroglutamic Acid (2-pyrrolidone-5 carboxylic acid) | 4 |
| Ethanol | 10 |
| DC Antiform H-10 | 0.03 |
| Sodium Benzoate | 0.2 |
| Tetrasodium EDTA | 0.1 |
| Sodium Chloride | 0.4 |
| Perfume | 0.01 |
| Water and minors | q.s. |
| NaOH or HCl for pH adjustment to pH = 3.0 | |

In a suitable container, the pyroglutamic acid, sodium chloride and water are added and mixed with stirring until mixture is homogeneous. Sodium benzoate, tetrasodium EDTA and ammonium lauryl sulfate are then added to the mixture with stirring and mixed until the ingredients are completely dissolved. Once dissolved, the benzalkonium chloride and DC Antiform H-10 are added to the mixture with stirring. In a separate container, the perfume and ethanol are mixed to form a premix. The premix is then added to the benzalkonium chloride mixture to form the aqueous lotion. The aqueous lotion is pH adjusted to about 3.0 using NaOH or HCl. The aqueous lotion is applied to the skin in an appropriate amount to disinfect and cleanse the skin.

Alternatively, the aqueous lotion can be applied onto the substrate of Example 1 at a lotion to wipe weight ratio of about 2:1 using conventional substrate coating techniques for application to the skin as an antimicrobial and cleansing wipe.

Example 4

An aqueous lotion was made based on the following composition:

| Ingredient | Amount (weight percent) |
| --- | --- |
| Benzalkonioum Chloride | 0.1 |
| Ammonium Lauryl Sulfate | 0.6 |
| Pyroglutamic Acid | 4 |
| (2-pyrrolidone-5 carboxylic acid) | |
| Ethanol | 10 |
| DC Antiform H-10 | 0.03 |
| Sodium Benzoate | 0.2 |
| Tetrasodium EDTA | 0.1 |
| Sodium Chloride | 0.4 |
| Tospearl 2000 | 2 |
| Perfume | 0.01 |
| Water and minors | q.s. |
| NaOH or HCl for pH adjustment to | |
| pH = 3.0 | |

In a suitable container, the pyroglutamic acid, sodium chloride and water are added and mixed with stirring until mixture is homogeneous. Sodium benzoate, tetrasodium EDTA and ammonium lauryl sulfate are then added to the mixture with stirring and mixed until the ingredients are completely dissolved. Once dissolved, the benzalkonium chloride and DC Antiform H-10 are added to the mixture with stirring. In a separate container, the perfume and ethanol are mixed to form a premix. The premix is then added to the benzalkonium chloride mixture to form the aqueous lotion. Next, the Tospearl is added into the aqueous lotion with stirring until homogeneous. The aqueous lotion is pH adjusted to about 3.0 using NaOH or HCl. The aqueous lotion is applied to the skin in an appropriate amount to disinfect and cleanse the skin.
Alternatively, the aqueous lotion can be applied onto the substrate of example 1 at a lotion to wipe weight ratio of about 2:1 using conventional substrate coating techniques for application to the skin as an antimicrobial and cleansing wipe.

What is claimed is:

1. An antimicrobial cleansing composition, comprising:
   (a) from about 0.001% to about 5% by weight of an antimicrobial active selected from the group consisting of benzalkonium chloride, N-(3-chloroallyl) hexaminium chlorides, methylbenzathonium; 2,4,4'-trichloro-2'-hydroxy-diphenyl ether; 3,4,4'-Trichlorocarbanilides; zinc pyrithione; para-chloro-meta-xylenol; and mixtures thereof;
   (b) from about 0.01% to about 20% by weight of an amphoteric surfactant;
   (c) from about 0.1% to about 20% by weight of 2-pyrrolidone-5 carboxylic acid; and
   (d) from about 3% to about 99% by weight of an aqueous component,
wherein the composition has a pH in the range of about 2.0 to about 5.5.

2. An antimicrobial cleansing composition according to claim 1 wherein the antimicrobial active is selected from the group consisting of Benzalkonium Chloride, Di($C_6$–$C_{14}$) alkyl di short chain ($C_{1-4}$ alkyl and/or hydroxyalkyl), N-(3-chloroallyl) hexaminium chlorides, Methylbenzethonium and mixtures thereof.

3. An antimicrobial cleansing composition according to claim 2 wherein the antimicrobial active is Benzalkonium chloride.

4. An antimicrobial cleansing composition according to claim 1 wherein the amphoteric surfactant is selected from surfactant compounds of the following formula(s):

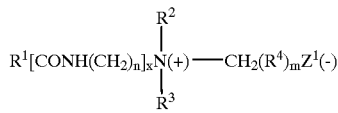

(I)

wherein $R^1$ is an alkyl, alkenyl, aryl, or hydroxyalkyl radical of from about 8 to about 22 carbon atoms, optionally interrupted with up to about 10 ethylene oxide moieties and/or 1 glyceryl moiety, $R^2$ and $R^3$ are individually selected from alkyl and monohydroxyalkyl groups containing from about 1 to about 3 carbon atoms, $R^4$ is alkylene, or hydroxyalkylene of from about 1 to about 4 carbon atoms, $Z^1$ is a radical selected from carboxylate, sulfonate, sulfate, phosphate, or phosphonate, x is 0 or 1, n is from about 1 to about 6, and m is 0 or 1.

5. An antimicrobial cleansing composition according to claim 4 wherein the amphoteric surfactant is selected from the group consisting of amide betaines, amide sulfo betaines, alkyl betaines, alkenyl betaines, sultaines (sulfo betaines), imidazolinium betaines, cocoamphocarboxypropionate, cocoamphocarboxypropionic acid, cocoamphocarboxyglycinate, cocoamphoacetate, N-lauryl-beta-amino propionic acid, N-lauryl-beta-imino-dipropionic acid, amine oxides, tertiary phosphine oxides, dialkyl sulfoxides, salts thereof and mixtures thereof.

6. An antimicrobial cleansing composition according to claim 4 wherein the amphoteric surfactant has the following formula:

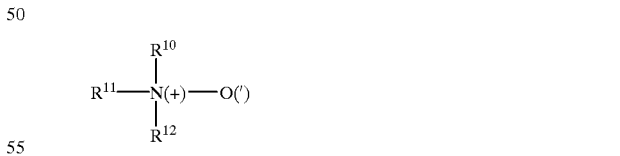

wherein $R^{10}$ or $R^{12}$ is methyl, ethyl, or hydroxyethyl, and $R^{11}$ is $C_8$–$C_{22}$ alkyl, alkenyl, or aryl, or $CH_3(CH_2)_p CONH(CH_2)_q$ wherein p is 8–22 and q is 1–6.

7. An antimicrobial cleansing composition according to claim 1 further comprising a mildness enhancer.

8. An antimicrobial cleansing composition according to claim 7 wherein the mildness enhancer is selected from the group consisting of cationic and nonionic polymers, co-surfactants, moisturizers and mixtures thereof.

9. An antimicrobial cleansing composition according to claim 8 wherein the moisturizer is a lipid skin moisturizer.

10. An antimicrobial cleansing composition according to claim 9 wherein the lipid skin moisturizer is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils, blends of liquid digestible or nondigestible oils with solid polyol polyesters, acetoglyceride esters, alkyl esters, alkenyl esters, lanolin and its derivatives, milk tri-glycerides, wax esters, beeswax derivatives, sterols, phospholipids and mixtures thereof.

11. An antimicrobial cleansing composition according to claim 10 wherein the lipid skin moisturizer is Petrolatum.

12. A method for cleansing and disinfecting skin comprising the applying a safe and effective amount of the composition of claim 1 on mammalian skin.

13. An antimicrobial cleansing wipe, comprising:
   (a) one or more layers of water-insoluble substrate; and
   (b) a safe and effective amount of antimicrobial cleansing composition, comprising by weight of the antimicrobial composition:
   (i) from about 0.001% to about 5% of an antimicrobial agent selected from the group consisting of benzalkonium chloride, N(3-chloroallyl) hexaminium chlorides, methylbenzethonium; 2,4,4'-trichloro-2'-hydroxydiphenyl ether; 3,4,4'-Trichlorocarbanilides; zinc pyrithione; para-chloro-meta-xylenol; and mixtures thereof;
   (ii) from about 0.01% to about 20% of an amphoteric surfactant:
   (iii) from about 0.1% to about 20% of 7-pyrrolidone-5 carboxylic acid; and
   (iv) from about 3% to about 99% of an aqueous component;
   wherein the composition has a pH in the range of about 2.0 to about 5.5.

14. A method for cleansing and disinfecting skin comprising the applying the antimicrobial cleansing wipe of claim 13 on mammalian skin.

* * * * *